United States Patent
Ingleton et al.

(10) Patent No.: US 10,353,377 B2
(45) Date of Patent: Jul. 16, 2019

(54) METHOD AND APPARATUS FOR MAPPING A REGION OF A BODY

(71) Applicant: BAE SYSTEMS plc, London (GB)

(72) Inventors: Martyn Ingleton, Rochester (GB); Jordan Henry Walker Jenkins, Rochester (GB); Tom Hon Pan Yip, Rochester (GB); Raife Edwin Thompson Norman, Rochester (GB)

(73) Assignee: BAE SYSTEMS plc, London (GB)

( * ) Notice: Subject to any disclaimer, the term of this patent is extended or adjusted under 35 U.S.C. 154(b) by 114 days.

(21) Appl. No.: 15/125,748

(22) PCT Filed: Mar. 10, 2015

(86) PCT No.: PCT/GB2015/050687
§ 371 (c)(1),
(2) Date: Sep. 13, 2016

(87) PCT Pub. No.: WO2015/136259
PCT Pub. Date: Sep. 17, 2015

(65) Prior Publication Data
US 2017/0010603 A1     Jan. 12, 2017

(30) Foreign Application Priority Data

Mar. 14, 2014  (EP) .................................. 14275061
Mar. 14, 2014  (GB) ................................. 1404527.2

(51) Int. Cl.
*G06F 19/00* (2018.01)
*G05B 19/4099* (2006.01)
(Continued)

(52) U.S. Cl.
CPC ........ *G05B 19/4099* (2013.01); *A61B 5/1077* (2013.01); *G01B 5/20* (2013.01);
(Continued)

(58) Field of Classification Search
CPC ...... G05B 19/4099; G05B 2219/49023; G06F 17/50; G06F 3/0346; G01B 7/003;
(Continued)

(56) References Cited

U.S. PATENT DOCUMENTS 3,945,122 A  *  3/1976  Durand ................ A61B 5/1077
33/512
2001/0032511 A1*  10/2001  Nagai .................. A61B 8/4281
73/618
(Continued)

FOREIGN PATENT DOCUMENTS

FR           2529776 A1      1/1984
WO             9740716      11/1997
WO         2015136259 A2     9/2015

OTHER PUBLICATIONS

Meunier, Pierre, et al. "Helmet accommodation analysis using 3D laser scanning." Applied Ergonomics 31.4: 361-369. (Year: 2000).*

(Continued)

*Primary Examiner* — Adam Lee
(74) *Attorney, Agent, or Firm* — Finch & Maloney PLLC

(57) ABSTRACT

A method of generating a topographic map of a region of a body for the manufacture of a body fitting article to be fitted to the region of the body. The method allows for the resultant topographical map of the body feature to be coupled to an anatomical and functional datum on the body. The method involves use of a contact probe which is configured to generate positional data which defines the surface it is drawn across. The method comprises the steps of urging a contact probe towards the outer surface of the body such that the contact probe is touching the outer surface of the body or separated from the outer surface of the body only by a barrier layer which is flattened against the outer surface of the body by the probe. The contact probe is drawn over the region of the body where the body fitting article is to be (Continued)

located such that the contact probe generates 3D positional data of the surface of the outer surface of the body in the region of the body where the body fitting article is to be located.

15 Claims, 3 Drawing Sheets

(51) Int. Cl.
| | |
|---|---|
| *A61B 5/107* | (2006.01) |
| *G01B 5/20* | (2006.01) |
| *G06F 3/0346* | (2013.01) |
| *G01B 7/00* | (2006.01) |
| *G06F 17/50* | (2006.01) |
| *A42C 2/00* | (2006.01) |
| *A61B 5/00* | (2006.01) |

(52) U.S. Cl.
CPC ........... *G01B 7/003* (2013.01); *G06F 3/0346* (2013.01); *G06F 17/50* (2013.01); *A42C 2/007* (2013.01); *A61B 5/6843* (2013.01); *G05B 2219/49023* (2013.01)

(58) Field of Classification Search
CPC ....... G01B 5/20; A61B 5/1077; A61B 5/6843; A42C 2/007
See application file for complete search history.

(56) References Cited

U.S. PATENT DOCUMENTS

| | | | |
|---|---|---|---|
| 2004/0163228 | A1 | 8/2004 | Piorkowsi et al. |
| 2006/0025685 | A1* | 2/2006 | dela Houssaye .... A61B 3/1005 600/443 |
| 2006/0055399 | A1* | 3/2006 | Georgeson ......... G01N 29/2481 324/232 |
| 2006/0101559 | A1 | 5/2006 | Moore, III et al. |
| 2009/0217763 | A1* | 9/2009 | Yamano ............... G01N 29/043 73/622 |
| 2011/0088476 | A1* | 4/2011 | Yamano ............... G01N 29/043 73/632 |
| 2011/0098722 | A1* | 4/2011 | Ulfarsson .............. A61B 5/055 606/130 |
| 2011/0203038 | A1* | 8/2011 | Jones, Jr. ............... A42B 3/125 2/411 |
| 2012/0285250 | A1* | 11/2012 | Rhim ...................... A61N 7/02 73/632 |
| 2014/0201889 | A1* | 7/2014 | Pietrzak ................ A42C 2/007 2/410 |

OTHER PUBLICATIONS

International Search Report and Written Opinion received for Patent Application No. PCT/GB2015/050687, dated May 30, 2016. 13 pages.
GB Intellectual Property Office Search Report under Section 17(5) received for GB Patent Application No. 1404527.2 dated Sep. 16, 2014. 3 pages.
GB Intellectual Property Office Search Report under Sections 17 and 18(3) received for GB Patent Application No. 1504018.1 dated Sep. 11, 2015. 6 pages.
Extended European Search Report received for EP Patent Application No. 14275061.1 dated Nov. 14, 2014. 9 pages.
Partial European Search Report received for EP Patent Application No. 14275061.1 dated Jun. 20, 2014. 5 pages.
International Preliminary Report on Patentability received for Patent Application No. PCT/GB2015/050687, dated Sep. 22, 2016. 11 pages.

* cited by examiner

METHOD AND APPARATUS FOR MAPPING A REGION OF A BODY

The present disclosure relates to a method for generating a map of a region of a body.

In particular the present disclosure is concerned with a method of, and apparatus for, generating a map of a region of a body for the manufacture of a body fitting article to be fitted to the region of the body.

Head mounted displays and other body mounted technology is known in the art. For example, it is common for pilots of modern military aircraft to be equipped with helmet mounted displays to help them perform their operational duties. The head mounted displays comprise an optical element, for example a visor, and a means for projecting additional information, in the form of graphics and/or text, onto the visor. Such head mounted apparel requires a custom fit liner to comfortably align the user's eyes to the optics during operation. This is especially important for manoeuvres involving 'high-g' loadings on a pilot, where the helmet could become detached or move relative to the pilot's head. Such misalignment could upset his/her use of the head mounted display, which must be aligned correctly with the user's eye to provide meaningful and accurate presentation of information, especially where the information being displayed is intended to be overlaid on the user's line of sight through the visor to reference the view through the visor.

It is known to measure head shape using a non-contacting laser scan method. However, this method does not make adequate compensation for hair style, volume and stiffness. Poor compensation of the effects of hair has led to discomfort, fit stability and misalignment issues.

Hence a means of providing a body fitting article which is less sensitive to the effects of body hair and results in a more accurately and comfortably fitting helmet liner is highly desirable.

SUMMARY

According to the present invention there is provided a method and apparatus as set forth in the appended claims. Other features of the invention will be apparent from the dependent claims, and the description which follows.

Accordingly there may be provided a method of generating a topographic map of a region of a body for the manufacture of a body fitting article to be fitted to the region of the body using a contact probe which is configured to generate positional data which defines the surface it is drawn across; the method comprising the steps of: urging a contact probe towards the outer surface of the body such that the contact probe is touching the outer surface of the body or separated from the outer surface of the body only by a barrier layer which is flattened against the outer surface of the body by the probe; and drawing the contact probe over the region of the body where the body fitting article is to be located such that the contact probe generates 3D positional data of the surface of the outer surface of the body in the region of the body where the body fitting article is to be located.

The barrier layer may comprise hair and/or a flexible close fitting material provided over the top of the body region to press body hair towards the body.

The method may further comprise: selecting a subset of the 3D positional data to define the topography of an interface surface of the body fitting article.

The method may further comprise: using the probe to generate the 3D positional data which defines a datum position on the body spaced apart from the region of the body where the body fitting article is to be located by touching the probe onto a pre-determined datum location.

The method may further comprise the steps of: locating a datum feature of the body with a reference fixture while the contact probe is urged towards the outer skin of the body and drawn over the region of the body where the body fitting article is to be located; the pre-determined datum location being the region of the reference feature which contacts the datum feature of the body.

The body fitting article may be a helmet and the region of a body may be a head.

The reference fixture may be an eye reference fixture configured to stabilise and immobilise the subject's head.

The datum feature of the body may be an eye socket.

The pre-determined datum location may be a sighting means with which the subject aligns their sight.

The 3D positional data may be acquired from the contact probe and processed to define the topography of the body region.

There may also be provided a method of manufacturing a body fitting article to be fitted to a region of a body comprising the steps of: generating a topographic map of a region of the body; and forming a region of a body fitting article in dependence upon the generated 3D positional data such that a region of the article conforms to the shape of the region the body where the body fitting article is to be located.

There may also be provided a method of manufacturing a custom fit liner for use in a helmet in dependence upon the topographical map generated by a method of the present disclosure, the liner being configured to align optics carried by the helmet with the eye line of a wearer of the helmet.

There may also be provided apparatus for performing a method of the present disclosure comprising: a contact probe having a contact surface for contacting the outer surface of the body, the contact surface being provided as sphere or truncated sphere; and a positional data transmitter element provided at the geometric centre of the sphere.

The apparatus may further comprise a reference fixture for stabilising and immobilising the region of a body while the contact probe is drawn over the region of the body where the body fitting article is to be located.

Hence there is provided a contact system for measuring a body part to enable the manufacture of a custom fit liner to fit within a standard helmet and thereby align the optical system carried by the helmet with the eyes of the wearer. The use of a contact method to measure user's head shape is configured to be insensitive to the effects of hair style, volume and stiffness.

BRIEF DESCRIPTION OF THE DRAWINGS

Examples of the present disclosure will now be described with reference to the accompanying drawings, in which.

DETAILED DESCRIPTION

The present disclosure relates to a method of generating a topographic map of a region of a body for the manufacture of a body fitting article to be fitted to the region of the body, including a method of collection of positional data required to generate the topographic map. The present disclosure also relates to a method of designing a body part fitting article to be fitted to a region of a body. In the non-limiting examples described, the body part is a human head, and the body part fitting article is a helmet. The method and apparatus herein described provide a means to measure the 3-dimensional shape of a head to allow definition of a custom liner to fit a helmet comfortably and accurately over the subject's head.

Figure 1:
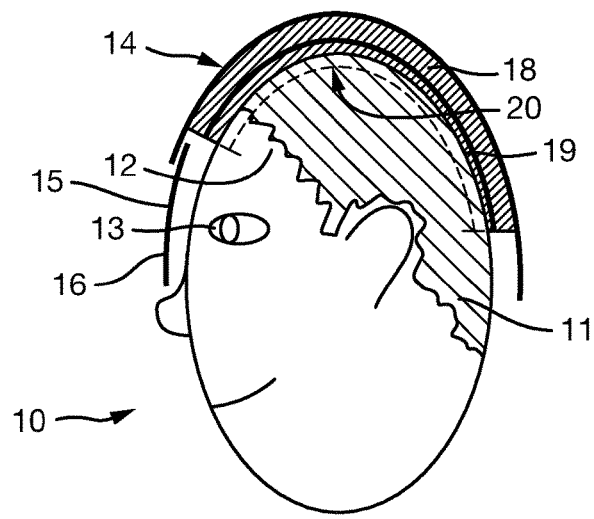
FIG. 1 shows a side view of a subject's head with a cross-sectional view of a helmet.

FIG. 1 shows a side view of a human subject's head 10, comprising hair 11, skin 12, eyes 13 with a cross-sectional view of a helmet 14 mounted on the head 10. The helmet 14 is fitted with a visor 15 which, as part of its structure, is provided with an optical display 16 to be combined with the subject's view through the visor 15, for example by projection onto a surface of the visor 15 for viewing by the subject. Examples of the visor 15 and optical display 16 and how they may be combined are well known and will not be described in detail in the present disclosure. However, the visor 15 is an integral part of the helmet 14, and the visor 15 must be located correctly relative to the subject's eyes 13 such that the subject can both see through the visor 15 to view his environment, and also have the information from the display 16 aligned correctly with the real world view of his environment through the visor 15. That is to say, the user's eyes and active "exit pupil" of the optical display must be aligned.

According to the method and apparatus of the present disclosure, a lining 18 is provided in the helmet 14 which conforms to the shape of the user's head 10 over a region 20 of the user's head 10 which will thus correctly locate the helmet 14 on the user's head 10. Spaced between the lining 18 and the users head is a "comfort" layer 19, which accommodates minor inconsistencies between the shape of the liner 18 and the subject's head, and may comprise a resilient foam or gel. The region 20, as shown, may span only part of the inner surface of the helmet 14. With such a lining 18 the helmet 14 will be inclined to locate in one position on the subjects head 10, and once fitted in place will be disinclined to move position relative to the head 10.

Figure 2:
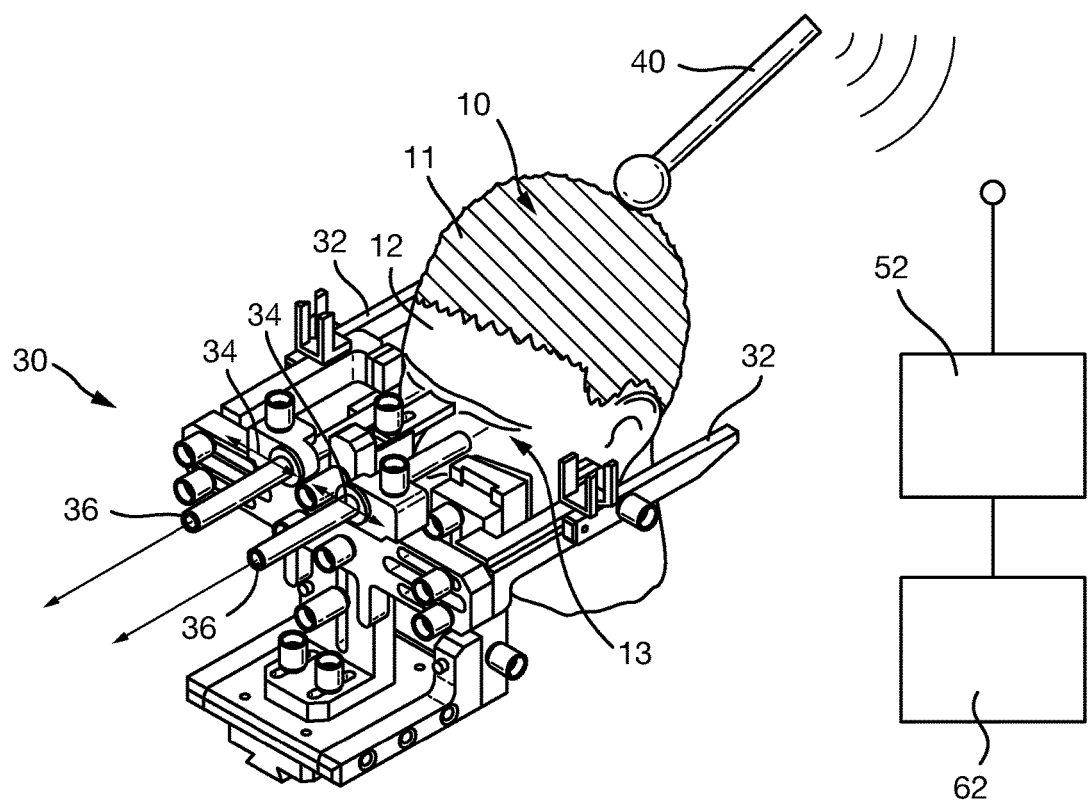
FIG. 2 shows a perspective view of a fixture according to the present disclosure with a subject's head in position.

FIG. 2 shows an eye reference fixture 30. The eye reference fixture 30 provides stabilisation features 32 to immobilise the head 10 and eye alignment features 34. The eye alignment features 34 may comprise sighting tubes 36, the axes of which are provided for line of sight and vertical, transverse eye alignment with side sighting blocks for the fore and/or aft position. The eye reference feature 30 may be mounted on any appropriate support structure (for example a table or tripod) that allows the reference fixture 30 to be comfortably located with respect to the subjects head 10 such that it will be possible for the head 10 to be kept static for the duration of a period required to operate the method of the present disclosure.

The sighting tubes 36 fitted to the reference fixture 30 are adjusted to suit the subject's Interpupillary Distance (IPD) prior to alignment. The sighting tubes 36 are configured such that a subject's head 10 may be positioned so the subject can to look through the sighting tubes 36 and the surface of the subject's corneas are located at the correct fore and/or aft separation from the subject-end surface of the tubes 36. In addition the Line Of Sight (LOS) of the sighting tubes can be adjusted to suit the Frankfurt Plane, chin to brow or any other anatomical reference.

For the avoidance of doubt, and as is well known, the Frankfurt plane (also called the auriculo-orbital plane) defines the normal "comfortable" direction that, under normal circumstances, a human will look/face.

Additional steadying features may also be provided as part of the fixture 30 for the positioning and support of brow, chin and cheek areas for the stabilisation of the subject's head.

Figure 3:
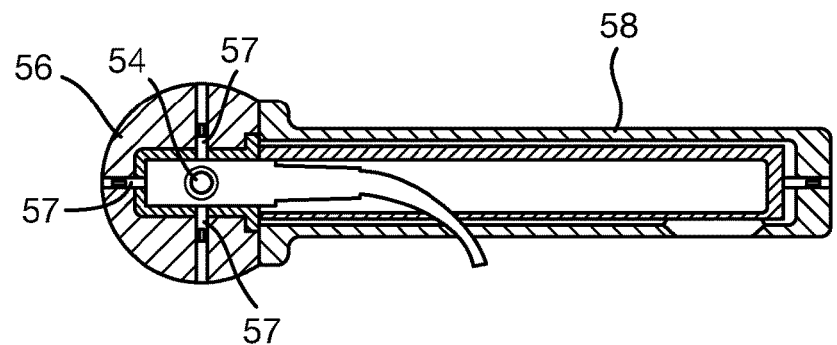
FIG. 3 shows a probe according the present disclosure.
Figure 4:
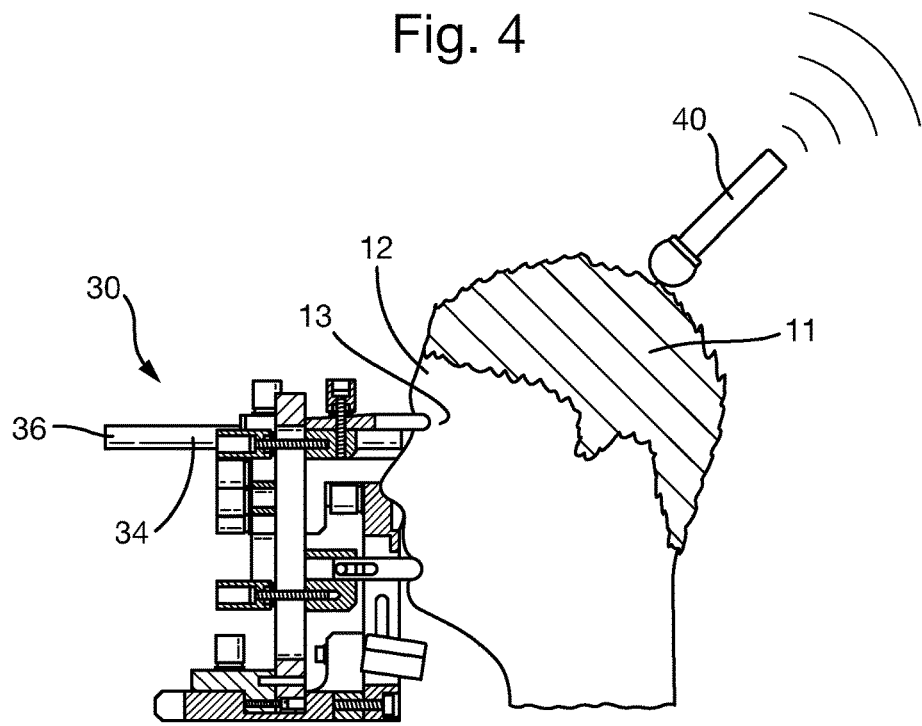
FIG. 4 shows a cross-sectional view of the fixture shown in FIG. 2.
Figure 5:
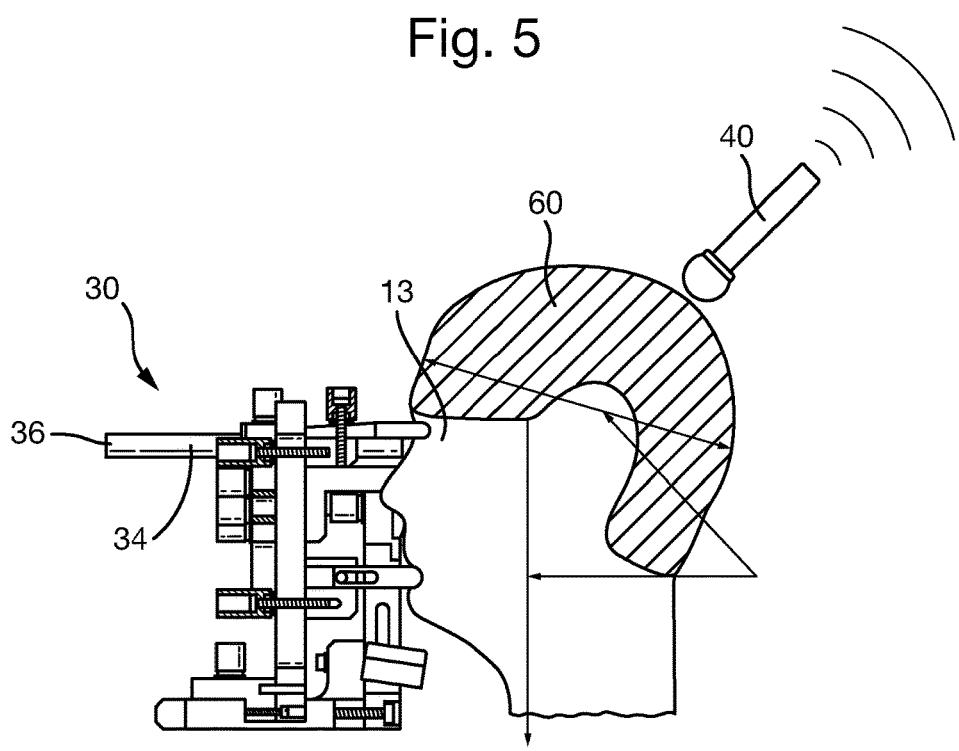
FIG. 5 shows a similar view to that in FIG. 4, with a cap according to the present disclosure fitted to the subject's head.

The apparatus of the present disclosure also comprises a probe 40 for collecting data about the shape of the subject's head 10, as shown in FIGS. 2, 4 and 5 and in more detail in FIG. 3. The probe 40 is a contact probe which is configured to generate 3D positional data which defines a surface it is drawn across. The probe 40 may be hand held, and has embedded therein one element 54 of a conventional magnetic position sensing system that cooperates with a unit 52 located at a fixed reference point arranged to receive signals transmitted by the element 54 from which a position and/or orientation for the probe 40 may be determined. Output from the receiver is converted into a stream of 6-Degree Of Freedom (DOF) data providing 3 translations and 3 angular terms.

In the example shown the probe 40 has a spherical measurement end 56, provided as a truncated sphere, and a grip portion 58 which is held by the operator. The positional signal transmitter 54 is positioned at the spherical centre of the end 56. In the example shown, grub screws 57 are provided to hold the positional signal transmitter 54 in place during assembly. Alternatively, or additionally, the transmitter 54 may also be held in place by an adhesive or cement. The transmitter 54 is positioned at the geometrical centre of the spherical end 56 so that, in use, angular terms defining the orientation of the sphere 56, and hence of the transmitter 54, can either be ignored or used for second order corrections during data processing, as required.

The probe end 56 is shaped to minimise contact errors with the underlying outer layer of the body part being probed, for example skin 12, hair 11, and locally to compress and part the subject's hair 11, where present.

The apparatus and method of the present disclosure may additionally comprise a cap 60 as shown in FIG. 5, to assess the contribution of hair 11 for a particular subject. The cap 60 is configured to be fitted over the subject's hair 11. The cap 60 is configured to be tensioned according to the mass supported by the helmet 14 and the reaction of any fitting system such as helmet straps. The cap 60 is further configured such that probing the outer surface of the cap 60 will provide, in combination with the results of a probing exercise without the cap 60 in place, an assessment of the offsets required to compensate for the volume, stiffness and style of the subjects hair. The use of the cap 60 is optional.

In operation, a subject places their head 10 in the reference fixture 30 as shown in FIGS. 2, 4, 5. The sighting tubes 36 fitted to the reference fixture 30 are adjusted to suit the subject's Interpupillary Distance (IPD) prior to alignment. The subject's head 10 is then positioned to look through the sighting tubes and the surface of the corneas located at the correct fore/aft separation from the subject-end surface of the tubes 36. In addition the Line Of Sight (LOS) of the sighting tubes 34 can be adjusted to suit the Frankfurt Plane, chin to brow or any other anatomical reference of the subject. Steadying features may then be positioned to the brow, chin and cheek areas to stabilise and immobilise the subject's head in the reference fixture 30.

Datum features of the body (in this example, eye socket 13) are located with the reference fixture 30 via the sighting tubes 34 while the contact probe 40 is urged towards (that is to say, placed into contact with) the outer surface of the body 10 and drawn over the region 20 of the body 10 where, in use, the helmet 14 is to be located. The phrase "outer surface of a body" is intended to refer to the outer skin, hair etc. of the body being mapped, whatever the outer surface layer may be. In examples where a body part other than a head is being probed for the design, manufacture and fitting of a body fitting article, the "outer surface of the body" can equally apply to nails or other features of body, or articles worn on the body.

The probe 40 is urged towards the outer skin 12 of the head (i.e. body part) 10 such that the contact probe is touching the outer skin 12 or separated from the outer skin 12 only by a barrier layer which is flattened against the outer skin 12 by the probe 40. The barrier layer may comprise hair 11 and/or a flexible close fitting material (for example the cap 60) provided over the top of the scanned body region to press body hair towards the body. With the subject suitably immobilised and aligned, the contact probe 40 is drawn over the region of the body 10 where the body fitting article is to be located such that the contact probe 40 generates 3D positional data of the surface of the outer surface of the skin 12 in the region 20 of the body 10 where the body fitting article 12 is to be located. The probe 40 should remain in contact with the subject, and urged towards the subject's outer layer (e.g. skin 12) throughout the process ensuring sufficient data is collected to define a complete surface. That is to say, the probe 40 is passed across the subject's head 10 making sure the spherical surface 56 is in constant contact at all times. The pressure applied to the probe 40 to head 10 interface during the head measurement process is either controlled by operator dexterity or a load cell in the grip 58 of the probe 40 to provide operator feedback. A combination of spherical form and pressure regulation provides the required accurate 3-dimensional map of the subject's scalp without excessive form errors from the presence of hair 11, while not discounting the contribution of the presence of hair 11 to the determination of the outer surface of the body where the hair cannot be easily parted and a layer of hair of a certain thickness will need to be taken into account in fitting a helmet 14 to the subject.

In one example, before, or after, probing the outer skin 12 of the head 10, parts of the reference fixture 30 are probed to provide three orthogonal datums relative to the subject's eyes. That is to say, the probe 40 is used to generate 3D positional data which defines a datum position on the body part 10, where the datum position is spaced apart from the region of the body 10 where the body fitting article (helmet 14) is to be located when worn by the subject. This is achieved by touching the probe 40 onto a pre-determined datum location. The pre-determined datum location is the region of the reference feature which contacts datum feature(s) of the body, which, for example could be either end of the sighting tubes 36.

In another example the receiver 52 may be provided in a fixed (or "known") position relative to the probe 40 and hence acts as a datum position to allow for determining the subject's eye position relative to probed region of the body, thereby obviating the need for probing the reference fixture 30 as defined above. However, the reference fixture 30 may still be probed to provide a confirmatory check in a method employing the receiver 52 as a datum.

In an alternative example, a receiver may be located at the centre of the end 56 of the probe 40, with a transmitter being provided as a separate unit to the probe 40, for example at a fixed (and optionally a "known") position relative to the probe 40.

The contact probing of the outer skin 12 of the head 10, as described above, may return information on body shape which is in part contaminated by the presence of hair 11. If required, the method may also include the step of assessing the contribution of hair for a particular subject by fitting the cap 60 over the hair 11, and tensioning the cap 60 according to the mass supported by the helmet and the reaction of any fitting system such as the nape. Probing the outer surface of the cap 60 in the same way as previously described then provides an assessment of the offsets required to compensate for the volume, stiffness and style of the subjects hair.

During the probing cycle 6-DOF (degrees of freedom) data relating to the location of the probe's spherical centre is continually recorded and stored for post processing. On completion of the head and optional reference fixture probing process, the acquired positional data set contains a cloud of data points which define the relative position of the scanned region of the head to the subject's eye position and/or reference fixture.

The probe motion data, continually recorded during the probing cycle, and datum information is transferred to the receiving unit 52, and then from the receiving unit 52 is communicated to a means for processing the data into a surface map, for example a computer. It may be transferred to Computer Aided Design (CAD) tool 62 for processing into a surface map of the head 10 with respect to the eye datums, as appropriate.

Alternatively, the data transferred to the receiving unit 52 could be transferred directly to a manufacturing tool for production of the body fitting apparel.

Figure 6:
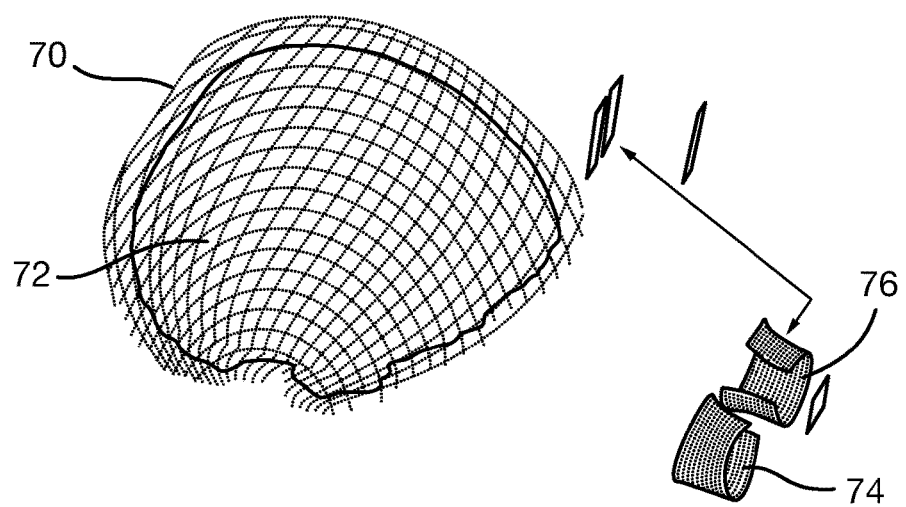
FIG. 6 shows a 2D representation of 3D topographical data representing the subject's scalp acquired using the method and equipment according to the present disclosure.

In the construction of a surface map, the positional data must be offset by the radius of the spherical probe 40 to determine the actual head surface topography. Features of the body fitting article must also be allowed for. In the example of a helmet, the thickness of comfort layer 19, lining material and hair thickness must be provided for in the offset in order to produce a correctly fitting helmet. The offset is indicated in FIG. 6, where the outer grid 70 indicates the co-ordinate data collected by the probe, and the lower/solid surface 72 indicates the surface 20 of the head 10. A subset of the 3D positional data obtained may be used to define the topography of the interface surface 20 of the body fitting article 14. The features 74, 76 in FIG. 6 represent the pre-determined datum location which, for example, is the end of the sighting tubes 36 distal to the subject's eyes 13.

The data is then used to form a region of a body fitting article (e.g. liner 18 of a helmet 14) in dependence upon the generated 3D positional data, such that the region 20 of the article (helmet) 14 conforms to the shape of the region 20 the body (head 10) where the body fitting article 14 is to be located.

Hence the invention uses a fixture 30 to locate features of the subject (e.g. the subject's eyes) and a roaming contact probe to measure the head shape. The probe 40 is linked to 3-dimensional metrology that records its motion relative to the eye location fixture. The probe locally parts and compresses the hair to minimise contact errors with the underlying skin. The probe can also be used to measure the surface of a head cap placed over the hair.

The above described apparatus may be employed as described in accordance with the present disclosure to measure the 3-dimensional shape of a head 10 (that is to say, a representation of the bald head of a subject) to allow definition of a custom liner 18 to fit a helmet 14 comfortably and accurately over the subject's head 10. That is to say, the method and apparatus of the present disclosure form part of a method of design and manufacture of a bespoke helmet tailored to the needs of an individual user.

The method and apparatus has been developed specifically for use with helmets containing optics (e.g. a helmet with an optical display system that requires alignment to the subject's eyes 13. However, the system (i.e. method an apparatus) could be adapted for alignment with any other anatomical feature, including features on the subject's head and other body parts.

The method and apparatus may be employed in the manufacture of head mounted displays and other body mounted technology.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method comprising:
   placing a contact probe in contact with either an outer surface of a region of a body or a barrier layer which is flattened against the outer surface of the region of the body by the contact probe, the contact probe being configured to generate, while the contact probe is drawn over the outer surface of the region of the body, a first set of 3D positional data which defines the outer surface of the region of the body, wherein a body fitting article is to be fitted over the outer surface of the region of the body;
   drawing the contact probe over the region of the outer surface of the region of the body where the body fitting article is to be fitted, such that the contact probe generates the first set of 3D positional data;
   touching a pre-determined datum location on a reference fixture with the contact probe to generate a second set of 3D positional data which defines a datum position on the body spaced apart from the region of the body where the body fitting article is to be fitted, wherein the first and second sets of 3D position data are different; and causing a computer aided design (CAD) tool to process a surface map based on the first and second sets of 3D positional data such that the surface map conforms to a shape of the region of the body where the body fitting article is to be fitted, or
   causing a manufacturing tool to manufacture the body fitting article according to the surface map, or both.

2. The method of claim 1 wherein placing the contact probe comprises placing the contact probe in contact with the barrier layer, the barrier layer comprising hair, a flexible close-fitting material provided over the region of the body to press hair towards the body, or both hair and the flexible close-fitting material.

3. The method of claim 1 wherein the method further comprises:
   selecting a subset of the first set of 3D positional data to define a topography of an interface surface of the body fitting article to be in contact with the outer surface of the region of the body while the body fitting article is fitted over the outer surface of the region of the body.

4. The method of claim 1 wherein the method further comprises:
   locating, via the reference fixture, a datum feature of the body positioned at the datum position, the reference fixture being in contact with the datum feature of the body and comprising a region that contacts the pre-determined datum location.

5. The method of claim 4 wherein the body fitting article is a helmet and the region of the body is a head.

6. The method of claim 5 wherein the reference fixture is an eye reference fixture configured to stabilize and immobilize the head.

7. The method of claim 5 wherein the datum feature of the body is an eye socket.

8. The method of claim 5 wherein the pre-determined datum location is a sighting means aligned with sight of a subject.

9. The method of claim 5, wherein the method further comprises:
   causing a custom-fit liner for use inside the helmet to be manufactured based on the first and second sets of 3D positional data, the custom-fit liner being configured to align optics integrated within the helmet with an eye line of a wearer of the helmet.

10. The method of claim 1 wherein the first and second sets of 3D positional data are acquired from the contact probe.

11. An apparatus comprising:
    a contact probe having a measurement end for contacting an outer surface of a region of a body, the measurement end being either a sphere or a truncated sphere, the contact probe being configured to
    generate, while the measurement end is drawn over the outer surface of the region of the body, a first set of 3D positional data which defines the outer surface of the region of the body, wherein a body fitting article is to be fitted over the outer surface of the region of the body, and
    generate, while the measurement end is touched to a pre-determined datum location on a reference fixture, a second set of 3D positional data which defines a datum position on the body spaced apart from the region of the body where the body fitting article is to be fitted, wherein the first and second sets of 3D positional data are different;

a 3D positional data transmitter element provided at a geometric center of the measurement end; and a receiving unit configured to
- cause a computer aided design (CAD) tool to process a surface map based on the first and second sets of 3D positional data such that the surface map conforms to a shape of the region of the body where the body fitting article is to be fitted, or
- cause a manufacturing tool to manufacture the body fitting article according to the surface map, or both.

12. The apparatus of claim 11 further comprising:
the reference fixture, wherein the reference fixture is configured to stabilize and immobilize the region of the body while the contact probe is drawn over the outer surface of the region of the body where the body fitting article is to be fitted.

13. The apparatus of claim 11 further comprising:
a computing system configured to process the first and second sets of 3D positional data from the 3D positional data transmitter element into the surface map.

14. The apparatus of claim 11 wherein the body fitting article is a helmet and the region of the body is a head.

15. The apparatus of claim 11, wherein
the receiving unit is further configured to receive the first and second sets of 3D positional data from the 3D positional data transmitter element.

* * * * *